(12) United States Patent
Moffitt

(10) Patent No.: US 7,742,819 B2
(45) Date of Patent: Jun. 22, 2010

(54) SYSTEM AND METHOD FOR UNIFORMLY DISPLACING A REGION OF NEURAL STIMULATION

(75) Inventor: Michael A. Moffitt, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 630 days.

(21) Appl. No.: 11/557,477

(22) Filed: Nov. 7, 2006

(65) Prior Publication Data

US 2008/0109048 A1   May 8, 2008

(51) Int. Cl.
*A61N 1/18* (2006.01)
(52) U.S. Cl. .............................. 607/46; 607/48; 607/117
(58) Field of Classification Search .................... 607/45, 607/46, 63–72, 117
See application file for complete search history.

(56) References Cited

U.S. PATENT DOCUMENTS

| | | | |
|---|---|---|---|
| 4,019,518 A | | 4/1977 | Maurer et al. |
| 4,379,462 A | * | 4/1983 | Borkan et al. ............... 607/117 |
| 4,424,812 A | | 1/1984 | Lesnick |
| 5,487,759 A | | 1/1996 | Bastyr et al. |
| 5,562,717 A | | 10/1996 | Tippey et al. |
| 6,002,966 A | * | 12/1999 | Loeb et al. .................... 607/57 |
| 6,219,580 B1 | * | 4/2001 | Faltys et al. .................. 607/57 |
| 6,289,247 B1 | * | 9/2001 | Faltys et al. .................. 607/57 |
| 6,393,325 B1 | | 5/2002 | Mann et al. |
| 6,944,503 B2 | | 9/2005 | Crowe et al. |
| 6,950,706 B2 | | 9/2005 | Rodriguez et al. |
| 6,999,820 B2 | | 2/2006 | Jordan |
| 2005/0209655 A1 | * | 9/2005 | Bradley et al. ............... 607/48 |
| 2005/0246003 A1 | | 11/2005 | Black et al. |
| 2006/0200219 A1 | | 9/2006 | Thrope et al. |

FOREIGN PATENT DOCUMENTS

| | | |
|---|---|---|
| GB | 2378903 A | 2/2003 |
| WO | WO03006106 | 1/2003 |

* cited by examiner

*Primary Examiner*—Carl H Layno
*Assistant Examiner*—Gary A Porter, Jr.
(74) *Attorney, Agent, or Firm*—Vista IP Law Group LLP

(57) ABSTRACT

A tissue stimulation system and computer software and method of operating the system is provided. An array of electrodes is placed contact with tissue of a patient (e.g., neural tissue), and electrical current is conveyed within the electrode array, thereby creating a stimulation region in the tissue. Electrical current is shifted between cathodes of the electrode array in incremental steps over a range, thereby causing displacement of the stimulation region at substantially uniform distances over the incremental steps. The electrical current may be shifted between the cathodes in accordance with a sigmoid-like function of a position of the stimulation region. A navigation table containing a series of states and corresponding gradually and non-uniformly changing electrical current values can be accessed, in which case, the electrical current may be shifted between the cathodes by incrementing through the states of the navigation table.

29 Claims, 10 Drawing Sheets

| Electrode Configuration | Electrode Number | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 1 | 0 | 100(−) | 100(+) | 0 | 0 | 0 | 0 | 0 | 0 | 0 | 0 | 0 | 0 | 0 | 0 | 0 |
| 2 | 0 | 0 | 0 | 0 | 100(−) | 0 | 0 | 0 | 0 | 0 | 0 | 0 | 100(+) | 0 | 0 | 0 |
| 3 | 0 | 0 | 30(−) | 0 | 0 | 45(+) | 0 | 0 | 0 | 0 | 70(−) | 0 | 0 | 55(+) | 0 | 0 |
| 4 | 15(+) | 0 | 15(−) | 21(−) | 0 | 21(+) | 0 | 0 | 22(+) | 0 | 22(−) | 42(−) | 42(−) | 42(+) | 0 | 0 |

*FIG. 1*

| Electrode Config. | Electrodes | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 271 | 0 | 0 | 0 | 1 | 0 | 0 | 0 | 0 | 0 | 0 | 0 | 0 | 1 | 0 | 0 | 0 |
| 272 | 0 | 0 | 0 | 0.95 | 0.05 | 0 | 0 | 0 | 0 | 0 | 0 | 0 | 1 | 0 | 0 | 0 |
| 273 | 0 | 0 | 0 | 0.9 | 0.1 | 0 | 0 | 0 | 0 | 0 | 0 | 0 | 1 | 0 | 0 | 0 |
| 274 | 0 | 0 | 0 | 0.85 | 0.15 | 0 | 0 | 0 | 0 | 0 | 0 | 0 | 1 | 0 | 0 | 0 |
| 275 | 0 | 0 | 0 | 0.8 | 0.2 | 0 | 0 | 0 | 0 | 0 | 0 | 0 | 1 | 0 | 0 | 0 |
| 276 | 0 | 0 | 0 | 0.75 | 0.25 | 0 | 0 | 0 | 0 | 0 | 0 | 0 | 1 | 0 | 0 | 0 |
| 277 | 0 | 0 | 0 | 0.7 | 0.3 | 0 | 0 | 0 | 0 | 0 | 0 | 0 | 1 | 0 | 0 | 0 |
| 278 | 0 | 0 | 0 | 0.65 | 0.35 | 0 | 0 | 0 | 0 | 0 | 0 | 0 | 1 | 0 | 0 | 0 |
| 279 | 0 | 0 | 0 | 0.6 | 0.4 | 0 | 0 | 0 | 0 | 0 | 0 | 0 | 1 | 0 | 0 | 0 |
| 280 | 0 | 0 | 0 | 0.55 | 0.45 | 0 | 0 | 0 | 0 | 0 | 0 | 0 | 1 | 0 | 0 | 0 |
| 281 | 0 | 0 | 0 | 0.5 | 0.5 | 0 | 0 | 0 | 0 | 0 | 0 | 0 | 1 | 0 | 0 | 0 |
| 282 | 0 | 0 | 0 | 0.45 | 0.55 | 0 | 0 | 0 | 0 | 0 | 0 | 0 | 1 | 0 | 0 | 0 |
| 283 | 0 | 0 | 0 | 0.4 | 0.6 | 0 | 0 | 0 | 0 | 0 | 0 | 0 | 1 | 0 | 0 | 0 |
| 284 | 0 | 0 | 0 | 0.35 | 0.65 | 0 | 0 | 0 | 0 | 0 | 0 | 0 | 1 | 0 | 0 | 0 |
| 285 | 0 | 0 | 0 | 0.3 | 0.7 | 0 | 0 | 0 | 0 | 0 | 0 | 0 | 1 | 0 | 0 | 0 |
| 286 | 0 | 0 | 0 | 0.25 | 0.75 | 0 | 0 | 0 | 0 | 0 | 0 | 0 | 1 | 0 | 0 | 0 |
| 287 | 0 | 0 | 0 | 0.2 | 0.8 | 0 | 0 | 0 | 0 | 0 | 0 | 0 | 1 | 0 | 0 | 0 |
| 288 | 0 | 0 | 0 | 0.15 | 0.85 | 0 | 0 | 0 | 0 | 0 | 0 | 0 | 1 | 0 | 0 | 0 |
| 289 | 0 | 0 | 0 | 0.1 | 0.9 | 0 | 0 | 0 | 0 | 0 | 0 | 0 | 1 | 0 | 0 | 0 |
| 290 | 0 | 0 | 0 | 0.05 | 0.95 | 0 | 0 | 0 | 0 | 0 | 0 | 0 | 1 | 0 | 0 | 0 |
| 291 | 0 | 0 | 0 | 0 | 1 | 0 | 0 | 0 | 0 | 0 | 0 | 0 | 1 | 0 | 0 | 0 |
| 292 | 0 | 0 | 0 | 0 | 0.95 | 0.05 | 0 | 0 | 0 | 0 | 0 | 0 | 1 | 0 | 0 | 0 |
| 293 | 0 | 0 | 0 | 0 | 0.9 | 0.1 | 0 | 0 | 0 | 0 | 0 | 0 | 1 | 0 | 0 | 0 |
| 294 | 0 | 0 | 0 | 0 | 0.85 | 0.15 | 0 | 0 | 0 | 0 | 0 | 0 | 1 | 0 | 0 | 0 |
| 295 | 0 | 0 | 0 | 0 | 0.8 | 0.2 | 0 | 0 | 0 | 0 | 0 | 0 | 1 | 0 | 0 | 0 |
| 296 | 0 | 0 | 0 | 0 | 0.75 | 0.25 | 0 | 0 | 0 | 0 | 0 | 0 | 1 | 0 | 0 | 0 |
| 297 | 0 | 0 | 0 | 0 | 0.7 | 0.3 | 0 | 0 | 0 | 0 | 0 | 0 | 1 | 0 | 0 | 0 |
| 298 | 0 | 0 | 0 | 0 | 0.65 | 0.35 | 0 | 0 | 0 | 0 | 0 | 0 | 1 | 0 | 0 | 0 |
| 299 | 0 | 0 | 0 | 0 | 0.6 | 0.4 | 0 | 0 | 0 | 0 | 0 | 0 | 1 | 0 | 0 | 0 |
| 300 | 0 | 0 | 0 | 0 | 0.55 | 0.45 | 0 | 0 | 0 | 0 | 0 | 0 | 1 | 0 | 0 | 0 |
| 301 | 0 | 0 | 0 | 0 | 0.5 | 0.5 | 0 | 0 | 0 | 0 | 0 | 0 | 1 | 0 | 0 | 0 |
| 302 | 0 | 0 | 0 | 0 | 0.45 | 0.55 | 0 | 0 | 0 | 0 | 0 | 0 | 1 | 0 | 0 | 0 |
| 303 | 0 | 0 | 0 | 0 | 0.4 | 0.6 | 0 | 0 | 0 | 0 | 0 | 0 | 1 | 0 | 0 | 0 |
| 304 | 0 | 0 | 0 | 0 | 0.35 | 0.65 | 0 | 0 | 0 | 0 | 0 | 0 | 1 | 0 | 0 | 0 |
| 305 | 0 | 0 | 0 | 0 | 0.3 | 0.7 | 0 | 0 | 0 | 0 | 0 | 0 | 1 | 0 | 0 | 0 |
| 306 | 0 | 0 | 0 | 0 | 0.25 | 0.75 | 0 | 0 | 0 | 0 | 0 | 0 | 1 | 0 | 0 | 0 |
| 307 | 0 | 0 | 0 | 0 | 0.2 | 0.8 | 0 | 0 | 0 | 0 | 0 | 0 | 1 | 0 | 0 | 0 |
| 308 | 0 | 0 | 0 | 0 | 0.15 | 0.85 | 0 | 0 | 0 | 0 | 0 | 0 | 1 | 0 | 0 | 0 |
| 309 | 0 | 0 | 0 | 0 | 0.1 | 0.9 | 0 | 0 | 0 | 0 | 0 | 0 | 1 | 0 | 0 | 0 |
| 310 | 0 | 0 | 0 | 0 | 0.05 | 0.95 | 0 | 0 | 0 | 0 | 0 | 0 | 1 | 0 | 0 | 0 |
| 311 | 0 | 0 | 0 | 0 | 0 | 1 | 0 | 0 | 0 | 0 | 0 | 0 | 1 | 0 | 0 | 0 |

*FIG. 2*

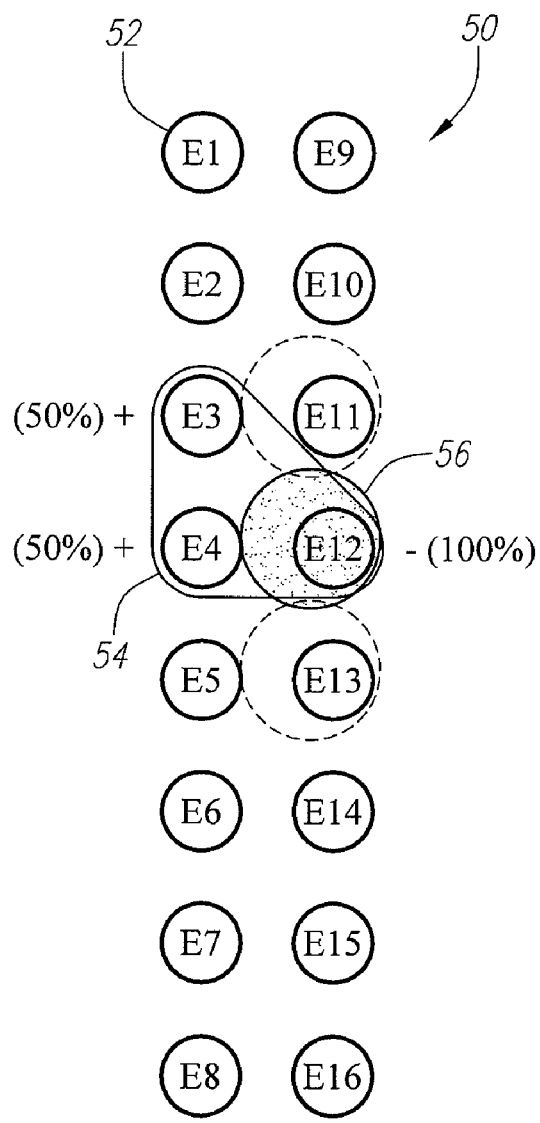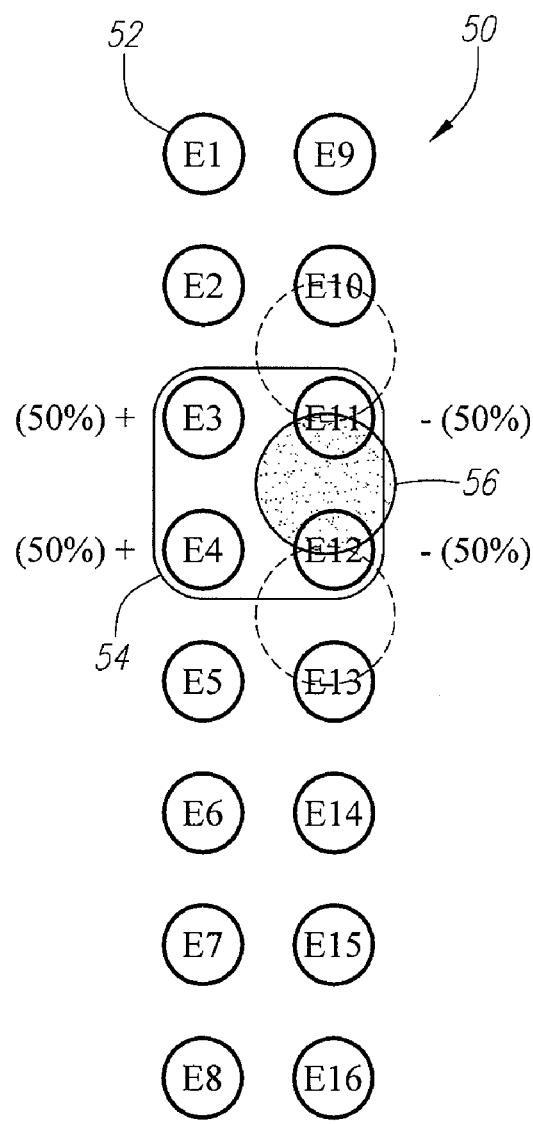
*FIG. 5*  *FIG. 6*

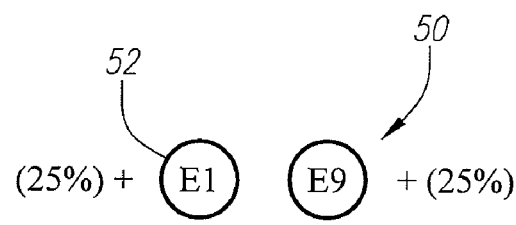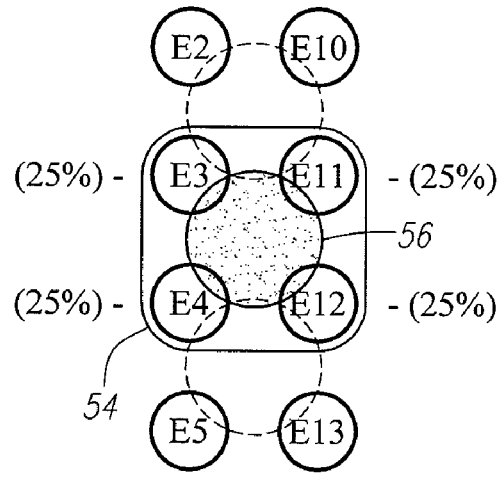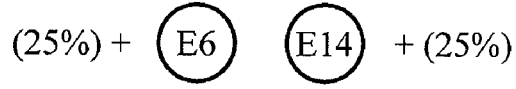
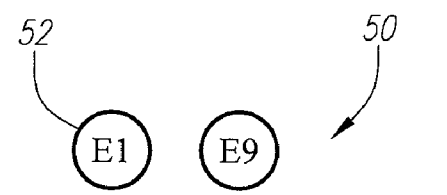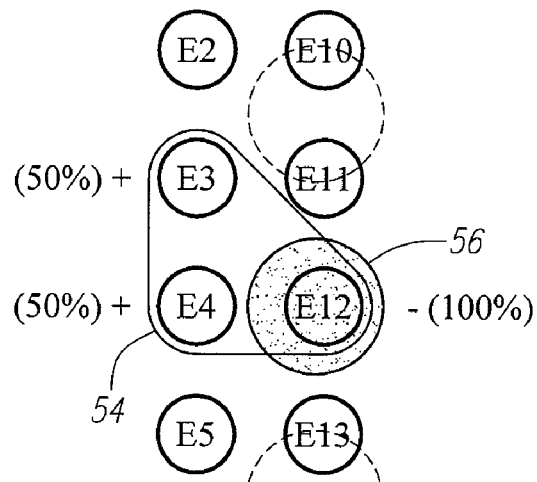
*FIG. 7*  *FIG. 8*

| State# | Cathode 1 (%) | Cathode 2 (%) |
|---|---|---|
| 1 | 100 | 0 |
| 2 | 77 | 23 |
| 3 | 70 | 30 |
| 4 | 66 | 34 |
| 5 | 63 | 37 |
| 6 | 60 | 40 |
| 7 | 58 | 42 |
| 8 | 56 | 44 |
| 9 | 54 | 46 |
| 10 | 52 | 48 |
| 11 | 50 | 50 |
| 12 | 48 | 52 |
| 13 | 46 | 54 |
| 14 | 44 | 56 |
| 15 | 42 | 58 |
| 16 | 40 | 60 |
| 17 | 37 | 63 |
| 18 | 34 | 66 |
| 19 | 30 | 70 |
| 20 | 23 | 77 |
| 21 | 0 | 100 |

*FIG. 11*

| State# | Cathode 1 (%) | Cathode 2 (%) | Cathode 3 (%) |
|---|---|---|---|
| 1 | 100 | 0 | 0 |
| 2 | 77 | 11.5 | 11.5 |
| 3 | 70 | 15 | 15 |
| 4 | 66 | 17 | 17 |
| 5 | 63 | 18.5 | 18.5 |
| 6 | 60 | 20 | 20 |
| 7 | 58 | 21 | 21 |
| 8 | 56 | 22 | 22 |
| 9 | 54 | 23 | 23 |
| 10 | 52 | 24 | 24 |
| 11 | 50 | 25 | 25 |
| 12 | 48 | 26 | 26 |
| 13 | 46 | 27 | 27 |
| 14 | 44 | 28 | 28 |
| 15 | 42 | 29 | 29 |
| 16 | 40 | 30 | 30 |
| 17 | 37 | 31.5 | 31.5 |
| 18 | 34 | 33 | 33 |
| 19 | 30 | 35 | 35 |
| 20 | 23 | 38.5 | 38.5 |
| 21 | 0 | 50 | 50 |

*FIG. 12*

SYSTEM AND METHOD FOR UNIFORMLY DISPLACING A REGION OF NEURAL STIMULATION

FIELD OF THE INVENTION

The present invention relates to tissue stimulation systems, and more particularly, to a system and method for programming an implantable tissue stimulator.

BACKGROUND OF THE INVENTION

Spinal cord stimulation (SCS) is a well-accepted clinical method for reducing pain in certain populations of patients. Spinal cord stimulator and other implantable tissue stimulator systems come in two general types: radio-frequency (RF)-controlled and fully implanted. The type commonly referred to as an "RF" system includes an external transmitter inductively coupled via an electromagnetic link to an implanted receiver-stimulator connected to one or more leads with one or more electrodes for stimulating tissue. The power source, e.g., a battery, for powering the implanted receiver, as well as control circuitry to command the receiver-stimulator, is contained in the external controller—a hand-held sized device typically worn on the patient's belt or carried in a pocket. Data/power signals are transcutaneously coupled from a cable-connected transmission coil placed over the implanted receiver-stimulator. The implanted receiver-stimulator receives the signal and generates the stimulation. In contrast, the fully implanted type of stimulating system contains the control circuitry, as well as a power supply, e.g., a battery, all within an implantable pulse generator (IPG), so that once programmed and turned on, the IPG can operate independently of external hardware. The IPG is turned on and off and programmed to generate the desired stimulation pulses from an external programming device using transcutaneous electromagnetic or RF links.

Whether an RF-controlled or fully implanted system is used, the electrode leads are implanted along the dura of the spinal cord. Individual wires within one or more electrode leads connect with each electrode on the lead. The electrode leads exit the spinal column and attach to one or more electrode lead extensions, when necessary. The electrode leads or extensions are typically tunneled along the torso of the patient to a subcutaneous pocket where the IPG or RF receiver-stimulator is implanted. The IPG or RF transmitter can then be operated to generate electrical pulses that are delivered, through the electrodes, to the dorsal column and dorsal root fibers within the spinal cord. The stimulation creates the sensation known as paresthesia, which can be characterized as an alternative sensation that replaces the pain signals sensed by the patient. Individual electrode contacts (the "electrodes") are arranged in a desired pattern and spacing in order to create an electrode array.

In order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. Once the leads are correctly positioned, a "fitting procedure" is performed by electronically programming the electrode array with a set of parameters that best addresses the painful site. Thus, electrode programming may be used to pinpoint the stimulation area correlating to the pain. Such electrode programming ability is particularly advantageous after implantation should the leads gradually or unexpectedly move, thereby relocating the paresthesia away from the pain site. With electrode programmability, the stimulation area can often be moved back to the effective pain site without having to reoperate on the patient in order to reposition the lead and its electrode array.

Electrodes can be selectively programmed to act as anodes (positive), cathodes (negative), or left off (zero). Other parameters that may be controlled or varied in SCS include the frequency of pulses provided through the electrode array, pulse width, and the amplitude of pulses delivered. Amplitude may be measured in milliamps, volts, etc., as appropriate, depending on whether the system provides stimulation from current sources or voltage sources. With some SCS systems, and in particular, SCS systems with independently controlled current or voltage sources, the distribution of the current to the electrodes (including the case of the pulse generator or receiver, which may act as an electrode) may be varied such that the current is supplied via numerous different electrode configurations. In different configurations, the electrodes may provide current (or voltage) in different relative percentages of positive and negative current (or voltage). Moreover, there may be some electrodes that remain inactive for certain electrode configurations, meaning that no current is applied through the inactive electrode. The number of electrodes available, combined with the ability to generate a variety of complex stimulation pulses, presents a huge selection of electrode configurations and electrical pulse parameters (together referred to as "sets of stimulation parameters") to the user.

To facilitate such selection, the physician or clinician generally programs the IPG, external controller, and/or external patient programmer through a computerized programming station or programming system. This programming system can be a self-contained hardware/software system, or can be defined predominantly by software running on a standard personal computer (PC). The PC or custom hardware can have a transmitting coil attachment to actively control the characteristics of the electrical stimulation generated by the IPG or transmitter to allow the optimum stimulation parameters to be determined based on patient feedback and for subsequently programming the IPG, external controller and/or external patient programmer with the optimum stimulation parameters.

A known practice for current-controlled stimulation systems is to select a few basic electrode configurations by selecting the polarity (anode, cathode, or inactive) and fractionalized current (percentage of current) sourced or sunk by each electrode either manually or automatically, and then refining these basic electrode configurations by gradually adjusting the polarity and fractionalized current flowing through the electrodes.

For example, FIG. 1 illustrates four different electrode configurations (using 16 electrodes) that can be tested. Each row specifies the polarity on each electrode. In exemplary electrode configuration 1, electrode 3 is an anode, electrode 2 is a cathode, and the remaining electrodes are inactive, with electrode 3 sourcing 100% of the current and electrode 2 sinking 100% of the current. In exemplary electrode configuration 2, electrode 13 is an anode, electrode 5 is a cathode, and the remaining electrodes are inactive, with electrode 13 sourcing 100% of the current and electrode 5 sinking 100% of the current. In exemplary electrode configuration 3, electrodes 6 and 14 are anodes, electrodes 3 and 11 are cathodes, and the remaining electrodes are inactive, with electrodes 6 and 14 respectively sourcing 45% and 55% percent of the current, and electrodes 3 and 11 respectively sinking 30% and 70% of the current. In exemplary electrode configuration 4, electrodes 1, 6, 9, and 14 are anodes, electrodes 3, 4, 11, and 12 are cathodes, and the remaining electrodes are inactive, with electrodes 1, 6, 9, and 14 respectively sourcing 15%, 21%, 22%, and 42%, and electrodes 3, 4, 11, and 12 respectively sinking 15%, 21%, 22%, and 42% of the current. Each of the basic electrode configurations creates a stimulation region having a nominal position within the spinal cord tissue.

Each of the basic electrode configurations can be refined by gradually moving the current sourced or sunk by the anodes and cathodes to adjacent electrodes, thereby electronically steering the stimulation region relative to the nominal position to determine the optimum refined electrode configuration. Electrical steering can be performed in accordance with a steering or navigation table. For example, as shown in FIG. 2, a portion of an exemplary navigation table can be used to gradually modify the exemplary basic stimulation set 2 of FIG. 1. As can be seen, exemplary electrode configuration 2 is represented by stimulation set 291 in FIG. 2. Current can be incrementally moved from cathode electrode 5 to cathode electrode 6 as one steps downward through the navigation table, and from cathode electrode 5 to cathode electrode 4 as one steps upward through the navigation table. The step size of the current should be small enough so that steering of the current does not result in discomfort to the patient, but should be large enough to allow refinement of a basic electrode configuration in a reasonable amount of time. In the illustrated embodiment, the current step size is 5%.

While the navigation table illustrated in FIG. 2 dictates that the current will be shifted between electrodes in uniform current steps, the stimulation region will actually move in non-uniform steps (i.e., the distance moved between steps is not uniform). This non-uniformity may cause some of the portions of the navigation table to be largely redundant in terms of clinical effect, while other portions of the navigation table may move the stimulation region in relatively large steps, potentially skipping useful electrode configurations. This hypothesis gains support from a computational model and anecdotal reports from the field. The model suggests that shifting current between anodes only minimally moves the stimulation region (<5% of movement of the stimulation region), and that much of the stimulation region movement occurs when shifting current between adjacent cathodes. Reports from the field also suggest that most of the paresthesia changes occur during shifts in current between the cathodes. The model also indicates that movement of the stimulation region during cathode current shifting is not linear. For example, the model predicts that nearly half of the stimulation region movement occurs when current is shifted between 60/40 and 40/60 splits in current percentage between two cathodes. That is, half of the movement of the paresthesia change may occur in only four navigation steps assuming a current shifting resolution of 5%. Thus, some portions of the navigation table may have too high of a current shifting resolution, thereby unnecessarily increasing navigation time, while other portions of the navigation table may have too low of a current shifting resolution, thereby ignoring potentially relevant electrode configurations.

There, thus, remains a need for an improved method and system for shifting current between electrical stimulation electrodes.

SUMMARY OF THE INVENTION

In accordance with the present inventions, a method of operating a tissue stimulation system is provided. In one method, the tissue stimulation system has multiple current-regulated outputs, although in alternative methods, the tissue stimulation system may have multiple voltage-regulated outputs. The method comprises placing an array of electrodes in contact with tissue of a patient (e.g., neural tissue), conveying an electrical current within the electrode array, thereby creating a stimulation region in the tissue, and shifting electrical current between cathodes of the electrode array in incremental steps over a range. The electrical current can be shifted between equal numbers of cathodes or between unequal numbers of cathodes. In one method, the electrical current is shifted between only two cathodes. One exemplary method further comprises implanting the electrode array adjacent the tissue, configuring a controller that generates an electrical current to be delivered to the electrode array, selecting an electrode configuration based on a therapeutic effect of the stimulation region as the electrical current is shifted between cathodes, and programming the controller with the electrode configuration.

In accordance with a first aspect of the present inventions, shifting the amplitude of the electrical current between cathodes of the electrode array causes displacement of the stimulation region at substantially uniform distances over the incremental steps. While the present inventions should not be so limited in their broadest aspects, by uniformly displacing the stimulation region, the number of incremental steps is minimized to expedite a testing process, while maximizing the possibility that all useful positions of the stimulation region are tested. This may be accomplished by making the incremental steps in current amplitude non-uniform. For example, the incremental steps at boundaries of the range over which the electrical current is shifted between the cathodes may be greater than the incremental steps at a center of the range. If the electrical current between the cathodes is fractionalized, the smallest increment step may be equal to or less than a certain percentage (e.g., two percent or five percent) and the greatest incremental step may be equal to or greater than a certain percentage (e.g., ten percent or twenty percent).

In accordance with a second aspect of the present inventions, the electrical current is shifted between the cathodes in accordance with a sigmoid-like function of a position of the stimulation region. While the present inventions should not be so limited in their broadest aspects, shifting electrical current between the cathodes in this manner provides for a more uniform displacement of the stimulation region over the incremental steps. In one method, the sigmoid-like function is an optimal sigmoid function. The electrical current may be fractionalized in the range of percentages set forth above.

In accordance with a third aspect of the present inventions, a navigation table containing a series of states and corresponding gradually and non-uniformly changing electrical current values is accessed. In this case, the electrical current is shifted between the cathodes by incrementing through the states of the navigation table. While the present inventions should not be so limited in their broadest aspects, using a navigation table provides a convenient means for gradually and non-uniformly shifting the electrical current between the cathodes. In one method, the differences between the electrical current values of adjacent states in the navigation table at boundaries of a range of states are greater than differences between adjacent electrical current values of adjacent states in the navigation table at a center of the range of states. If the electrical current values are fractionalized, the smallest difference between adjacent states in the navigation table may be equal to or less than a certain percentage (e.g., five percent or ten percent) and the greatest difference between adjacent states in the navigation table may be equal to or greater a certain percentage (e.g., ten percent or twenty percent).

The afore-described methods can be implemented in a computer readable medium. For example, the medium may contain instructions, which when executed, commands the electrical current to be conveyed within an electrode array, thereby creating a stimulation region in the tissue, and shifts the electrical current between the cathodes in incremental steps over the range.

The afore-described methods can also be implemented in a tissue stimulation system. The system may comprise an array of electrodes configured for being placed in contact with the tissue, a controller configured for conveying the electrical current within the electrode array, thereby creating the stimulation region in the tissue, and a processor coupled to the controller for shifting the electrical current between the cathodes in incremental steps over the range.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 1 is an exemplary table containing different electrode combinations that can be used in a Spinal Cord Stimulation (SCS) system;

FIG. 2 is an exemplary navigation table containing a series of electrode states and corresponding fractionalized current values between active electrodes;

FIG. 5 is a schematic view illustrating one manner of steering current in an electrode array;

FIG. 6 is a schematic view illustrating another manner of steering current in an electrode array;

FIG. 7 is a schematic view illustrating still another manner of steering current in an electrode array;

FIG. 8 is a schematic view illustrating yet another manner of steering current in an electrode array;

FIG. 11 is an exemplary navigation table containing a series of electrode states and corresponding fractionalized current values between active electrodes, which can be used by the SCS system of FIG. 3 to steer current in the electrode arrays of FIGS. 5-7; and FIG. 12 is an exemplary navigation table containing a series of electrode states and corresponding fractionalized current values between active electrodes, which can be used by the SCS system of FIG. 3 to steer current in the electrode array of FIG. 8.

DETAILED DESCRIPTION OF THE EMBODIMENTS

At the outset, it is noted that the present invention may be used with an implantable pulse generator (IPG), radio frequency (RF) transmitter, or similar electrical stimulator, that may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical and deep brain stimulator, peripheral nerve stimulator, or in any other neural stimulator configured to treat urinary incontinence, sleep apnea, shoulder sublaxation, etc.

Figure 3:
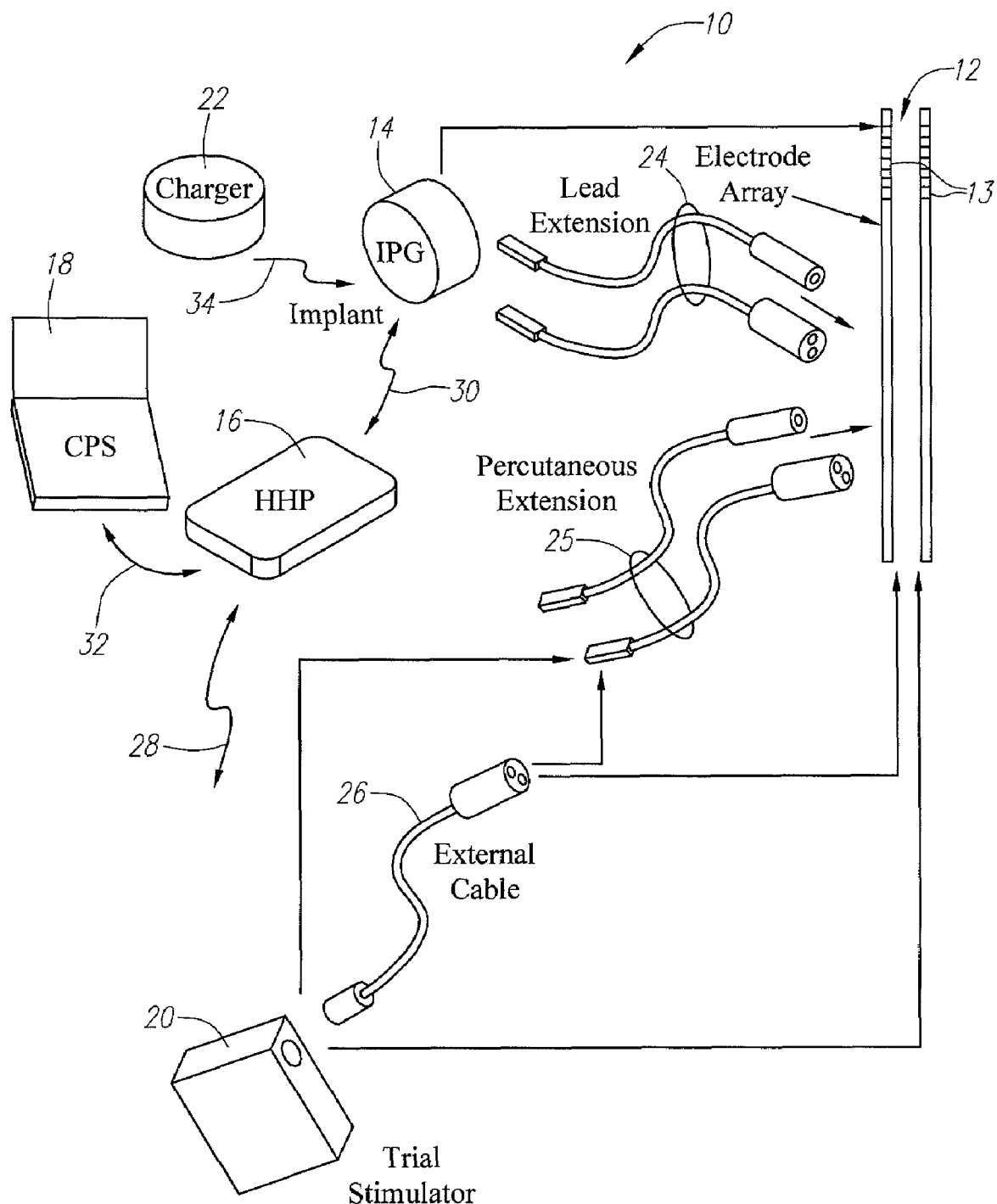
FIG. 3 is perspective view of one embodiment of a SCS system arranged in accordance with the present inventions.

Turning first to FIG. 3, an exemplary SCS system 10 generally includes one or more implantable electrode leads 12, an implantable pulse generator (IPG) 14 (or alternatively an external transmitter and RF receiver-stimulator), an external handheld programmer (HHP) 16, a Clinician's Programmer Station (CPS) 18, an External Trial Stimulator (ETS) 20, and an external charger 22.

The electrode leads 12 are implanted into the patient's spinal cord, and are physically connected either to the IPG via one or more percutaneous lead extensions 24, or to the ETS 20 via the percutaneous lead extensions 25 and external cable 26. The electrode leads 12 carry a plurality of electrodes arranged in an array 13. In the illustrated embodiment, two electrode leads 12 are provided, each carrying a column of eight electrodes. The IPG 14 and ETS 20, which have similar pulse generation circuitry, control the electrode array 13 with electrical stimulation pulses of varying amplitudes and widths and at different frequencies. The ETS 20 is a non-implantable device that is used on a trial basis after the electrode leads 12 have been implanted and prior to implantation of the IPG 14, to test the effectiveness of the stimulation that is to be provided. After implantation, the IPG 14 is used to provide the therapeutic stimulation under control of the patient.

The HHP 16 may be used to telemetrically control the ETS 20 via a bi-directional RF communications link 28. Once the IPG 14 and electrode leads 12 are implanted, the HHP 16 may be used to telemetrically control the IPG 14 via the RF communications link 30. Such control allows the IPG 14 to be turned on or off and to be programmed with different stimulation programs after implantation. The CPS 18 provides a clinician detailed stimulation parameters for programming the IPG 14 and ETS 20 in the operating room and in follow-up sessions. The CPS 18 may perform this function by indirectly communicating with the IPG 14 or ETS 20, through the HHP 16, via an IR communications link 32. Alternatively, the CPS 18 may directly communicate with the IPG 14 or ETS 20 via an RF communications link (not shown). The external charger 22 is a portable device used to transcutaneously charge the IPG 14 via an inductive link 34.

Figure 4:
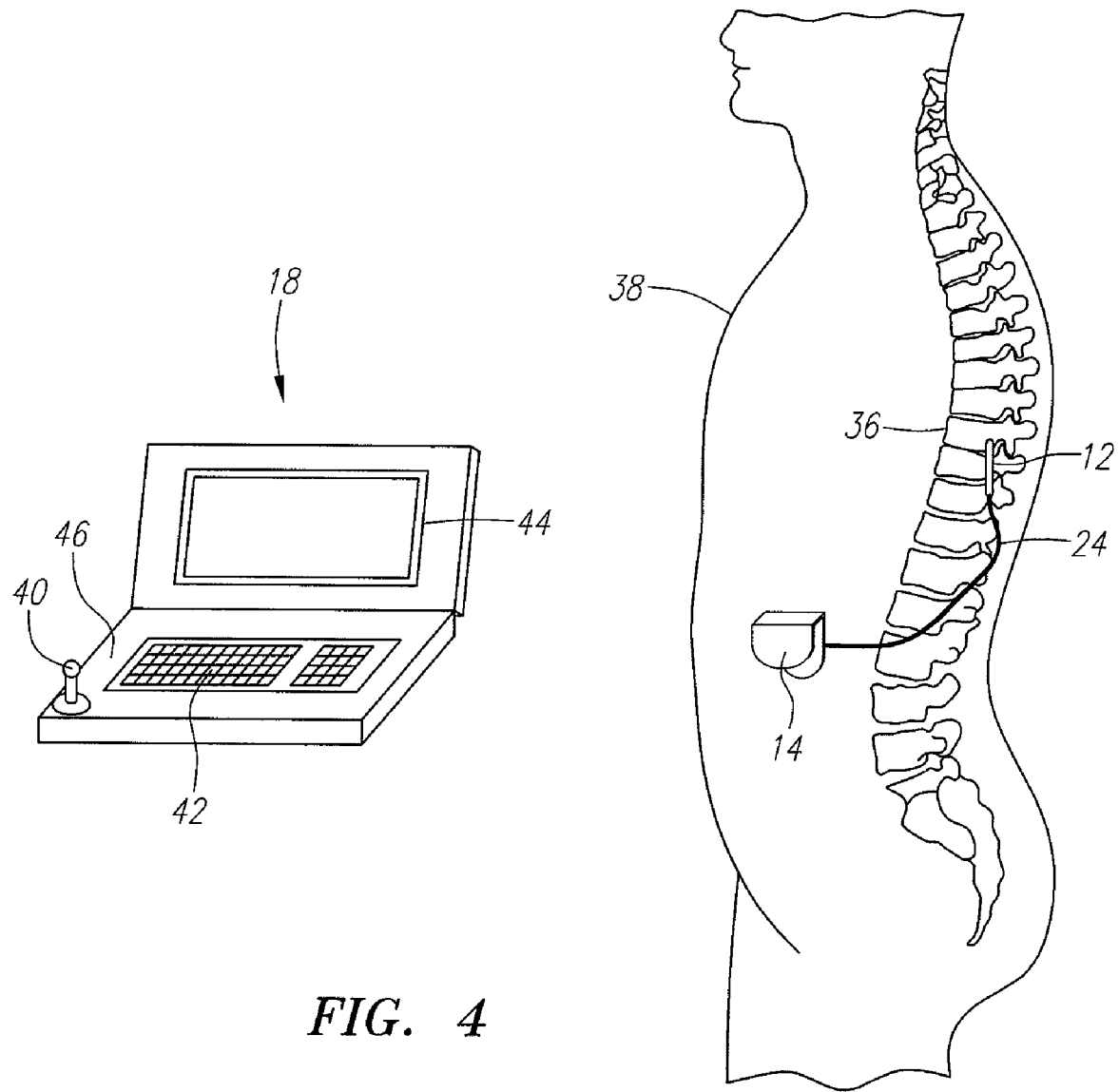
FIG. 4 is a plan view of the SCS system of FIG. 3 in use with a patient.

As shown in FIG. 4, the electrode leads 12 are implanted within the spinal column 36 of a patient 38. The preferred placement of the electrode leads 12 is adjacent, i.e., resting upon, the spinal cord area to be stimulated. Due to the lack of space near the location where the electrode leads 12 exit the spinal column 36, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12.

The IPG 14 includes a programmable memory used to direct electrical current to the electrode array 13. In the illustrated embodiment, IPG 14 can individually program the electrodes of the array 13. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention.

As briefly discussed above, modifying the parameters in the programmable memory of the IPG 14 after implantation is performed by a physician or clinician using the CPS 18, which can directly communicate with the IPG 14 or indirectly communicate with the IPG 14 via the HHP 16. That is, the CPS 18 can be used by the physician or clinician to modify operating parameters of the electrode array 13 near the spinal cord. In the illustrated embodiment, the CPS 18 includes a joystick 40, a keyboard 42, and a programming display screen 44 housed in a case 46. It is to be understood that in addition to, or in lieu of, the joystick 40, other directional programming devices may be used, such as a mouse, or directional keys included as part of the keys associated with the keyboard 42.

As shown in FIG. 4, the overall appearance of the CPS 18 is that of a laptop personal computer (PC), and in fact, may be implanted using a PC that has been appropriately configured to include a directional-programming device and programmed to perform the functions described herein. Thus, the programming methodologies can be performed by executing software instructions contained within the CPS 18. Alternatively, such programming methodologies can be performed using firmware or hardware. In any event, the CPS 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

The CPS 18 greatly simplifies the programming of multiple electrode configurations, allowing the physician or clinician to readily determine a desired combination of electrodes, i.e., a selected group of electrodes, using the joystick 40 or other directional programming device that affects which electrodes are selected, the polarity of individual electrodes, and the stimulation intensity distribution, all of which parameters can contribute to "steer" and/or "focus" the stimulation current to modify the size and location of a stimulation region during neural stimulation, as will be described in further detail below. Advantageously, as the stimulating group of electrodes is being configured and positioned using the directional signals generated by the joystick 40, the programmed stimulation is automatically directed to the electrode array 13 for immediate and continuous patient response. Based on this feedback, one or more electrode configurations can be selected and programmed into the IPG 14 (or ETS 20).

Referring to FIG. 5, an array of electrodes 50 is shown arranged in two columns of eight electrodes 52. The electrode array 50 comprises a stimulating group of electrodes 54 having two electrodes in the left column (electrodes E3 and E4) set to a "+" polarity (i.e., as anodes), and one electrode in the right column (electrode E12) set to a "−" polarity (i.e., as a cathode). This polarity and grouping creates an electric field, which will cause electrical current to flow from both electrodes E3 and E4 to the single electrode E12, which in turn results in a single stimulation region 56 (shown as a solid circle) that is nearer to the right column than the left column, and that tends to be more concentrated nearer the electrode E12.

The joystick 40 can move the stimulating group of electrodes 54 up and down within the array 52, which thus moves the stimulation region 56 up or down the spinal cord respectively. As the joystick 40, or other directional input device, is maneuvered forward, for example, the stimulation region 56 is steered up the spinal cord. This occurs, in one embodiment, by moving the group of stimulating electrodes 54 up one row along the array 52. As the joystick 40, or other directional input device, is maneuvered rearward, for example, the stimulation region 56 is steered down the spinal cord. This occurs, in one embodiment, by moving the group of stimulating electrodes 54 down one row along the array 52. Because stimulation is generally associated with cathodes (or negative polarity electrodes), the stimulation can also be distributed among a group of electrodes by changing positive polarities to negative, and negative to positive, in the path of the direction programming within the group.

For even finer control of current steering, as the joystick 40 moves the stimulation area in an upward direction, the amplitude distribution is graduated to higher cathodes until the lower cathodes are eventually turned off, after which the next higher cathodes start increasing in amplitude as the joystick 40 is held in the forward position. Likewise, as the joystick 40 moves the stimulation area in a downward direction, the amplitude distribution is graduated to lower cathodes until the upper cathodes are eventually turned off, after which the next lower cathodes start increasing in amplitude as the joystick 40 is held in the forward position.

Notably, in standard electrode configurations, movement of the anodes does not have a significant impact on the movement of the stimulation region. However, in medial-lateral electrode configurations such as that shown in FIG. 5, anode current may have a significant impact on the movement of the stimulation region. Thus, in the case of FIG. 5, amplitude distribution may be graduated to higher anodes until the lower anodes are eventually turned off to shift the stimulation region. For purposes of simplicity, however, we describe gradual shifting of the cathode currents, while maintaining the same current at the anodes, to control the position of the stimulation region in all of the examples set forth hereafter.

Assuming that the stimulating electrode group 54 is assigned a "group amplitude," which is the absolute value total for all of the cathodes (-electrodes) in a single stimulating group), the default fractionalized current value for such group 54 might be 100% on the cathode (i.e., electrode E12) and 50% on each anode (i.e., electrodes E3, E4).

As the joystick 40 is moved forward, causing electrode E11 to be included within the stimulating electrode group 54, and electrode E12 to be excluded from the stimulating electrode group 54, the fractionalized current flowing through electrode E11 increases toward 100%, while the fractionalized current flowing through electrode E12 decreases toward 0%. As a result, the stimulation region 56 moves from its initial position adjacent electrode E12 to a subsequent position adjacent electrode E11 (shown as a dashed circle).

As the joystick 40 is moved rearward, causing electrode E13 to be included within the stimulating electrode group 54, and electrode E12 to be excluded from the stimulating electrode group 54, the fractionalized current through electrode E13 increases toward 100%, while the fractionalized current through electrode E12 decreases toward 0%. As a result, the stimulation region 56 moves from its initial position adjacent electrode E12 to a subsequent position adjacent electrode E13 (shown as a dashed circle). In this manner, the joystick 40 is able to steer the stimulation region 56 up or down to a desired stimulation area.

Note that the stimulation region 56 may also be steered in this manner left or right, although this is only possible when there are at least two columns of electrodes. In addition, while steering of the stimulation region 56 has been described in the context of two columns electrodes, the stimulation region 56 may also be steered in the context of a single column of electrodes. For example, if electrodes E9 and E15 (instead of electrodes E3 and E4) are set to a "+" polarity (i.e., as anodes), the stimulation region 56 may be steering up or down in the same manner described above with respect to FIG. 5.

Of course, a stimulating electrode group may have more than one cathode. For example, referring to FIG. 6, a stimulating group of electrodes 54 has two electrodes in the left column (electrodes E3 and E4) set to a "+" polarity (i.e., as anodes), and two electrodes in the right column (electrode E11 and E12) set to a "−" polarity (i.e., as cathodes). This polarity and grouping creates an electric field, which will cause electrical current to flow from both electrodes E3 and E4 to both electrodes E11 and E12, which results in a single stimulation region 56 that is nearer to the right column than the left column, and that tends to be more concentrated between electrodes E11 and E12. Assuming that the stimulating electrode group 54 is assigned a group amplitude, the default fractionalized current value for such group 54 might be 50% on each cathode (i.e., electrodes E11, E12) and 50% on each anode (i.e., electrodes E3, E4).

As the joystick 40 is moved forward, causing electrode E12 to be excluded from the stimulating electrode group 54, the fractionalized current though electrode E11 increases toward 100%, while the fractionalized current through electrode E12 decreases toward 0%. As soon as the fractionalized current flowing through electrode E12 reaches 0%, the fractionalized current through electrode E10 begins to increase toward 100%, while the fractionalized current through electrode E11 decreases toward 0%. When the fractionalized current through electrode E10 has been increased to 50%, and the fractionalized current through electrode E11 has been decreased to 50%, the stimulation region 56 will have moved from its initial position between electrodes E11 and E12 to a subsequent position between electrodes E11 and E10 (shown as a dashed circle).

Similarly, as the joystick 40 is moved rearward, causing electrode E11 to be excluded from the stimulating electrode group 54, the fractionalized current though electrode E12 increases toward 100%, while the fractionalized current through electrode E11 decreases toward 0%. As soon as the fractionalized current flowing through electrode E11 reaches 0%, the fractionalized current through electrode E13 begins to increase toward 100%, while the fractionalized current through electrode E12 decreases toward 0%. When the fractionalized current through electrode E13 has been increased to 50%, and the fractionalized current through electrode E12 has been decreased to 50%, the stimulation region 56 will have moved from its initial position between electrodes E11 and E12 to a subsequent position between electrodes E12 and E13 (shown as a dashed circle).

A stimulating electrode group may have more cathodes in two columns. For example, referring to FIG. 7, a stimulating group of electrodes 54 has two electrodes in the left column (electrodes E1 and E6) and two electrodes in the right column (electrodes E9 and E14) set to a "+" polarity (i.e., as anodes), and two electrodes in the left column (electrodes E3 and E4) and two electrodes in the right column (electrodes E11 and E12) set to a "−" polarity (i.e., as cathodes). This polarity and grouping creates an electric field, which will cause electrical current to flow from electrodes E1, E6, E9, and E14 to electrodes E3, E4, E11, and E12, which in turn results in a single stimulation region (shown as a solid circle) that is centered between the left and right columns, and that tends to be more concentrated between electrodes E3, E4, E11 and E12. Assuming that the stimulating electrode group 54 is assigned a group amplitude, the default fractionalized current value for such group 54 might be 25% on each cathode (i.e., electrodes E3, E4, E11, E12) and 25% on each anode (i.e., electrodes E1, E6, E9, and E14).

As the joystick 40 is moved forward, causing electrodes E4 and E12 to be excluded from the stimulating electrode group 54, the fractionalized current though each of electrodes E3 and E11 increases toward 50%, while the fractionalized current through each of electrodes E4 and E12 decreases toward 0%. As soon as the fractionalized current flowing through each of electrodes E4 and E12 reaches 0%, the fractionalized current through each of electrodes E2 and E10 begins to increase toward 50%, while the fractionalized current through each of electrodes E3 and E11 decreases toward 0%. When the fractionalized current through each of electrodes E2 and E10 has been increased to 25%, and the fractionalized current through each of electrodes E3 and E11 has been decreased to 25%, the stimulation region 56 will have moved from its initial position between electrodes E3, E4, E11, and E12 to a subsequent position between electrodes E2, E3, E10, and E11 (shown as a dashed circle).

Similarly, as the joystick 40 is moved rearward, causing electrodes E3 and E11 to be excluded from the stimulating electrode group 54, the fractionalized current though each of electrodes E4 and E12 increases toward 100%, while the fractionalized current through each of electrodes E3 and E11 decreases toward 0%. As soon as the fractionalized current flowing through each of electrodes E3 and E11 reaches 0%, the fractionalized current through each of electrodes E5 and E13 begins to increase toward 50%, while the fractionalized current through each of electrodes E4 and E12 decreases toward 0%. When the fractionalized current through each of electrodes E5 and E13 has been increased to 25%, and the fractionalized current through each of electrodes E4 and E12 has been decreased to 25%, the stimulation region 56 will have moved from its initial position between electrodes E3, E4, E11, and E12 to a subsequent position between electrodes E4, E5, E12, and E13 (shown as a dashed circle).

While the previous examples have illustrated the shifting of current between equal sets of cathodes (e.g., from a single cathode to another single cathode electrode, or from two cathodes to another two cathodes), current can be shifted between unequal sets of cathodes (e.g., from a single cathode to multiple cathodes or from multiple cathodes to a single cathode). Preferably, during shifting of current between sets of cathodes, the single stimulation region 56 does not disperse into multiple stimulation regions. Thus, as long as the distance between the cathode(s) to which the current is shifted is relatively small (if more than one cathode) and as long as the distance between the cathode(s) to which the current shifted and the cathode(s) from which the current is shifted is relatively small, current can be shifted between any combination of cathodes without affecting the integrity of the single stimulation region 56.

As one example, referring to FIG. 8, a stimulating group of electrodes 54 has two electrodes in the left column (electrodes E3 and E4) set to a "+" polarity (i.e., as anodes), and one electrode in the right column (electrode E12) set to a "−" polarity (i.e., as a cathode). In the same manner described above with respect to FIG. 5, this polarity and grouping creates an electric field, which will cause electrical current to flow from both electrodes E3 and E4 to electrode E12, which results in a single stimulation region 56 that is nearer to the right column than the left column, and that tends to be more concentrated adjacent electrode E12. Assuming that the stimulating electrode group 54 is assigned a group amplitude, the default fractionalized current value for such group 54 might be 100% on the cathode (i.e., electrode E12) and 50% on each anode (i.e., electrodes E3, E4).

As the joystick 40 is moved forward, causing electrodes E10 and E11 to be included within the stimulating electrode group 54, and electrode E12 to be excluded from the stimulating electrode group 54, the fractionalized current through each of electrodes E10 and E11 increases toward 50%, while the fractionalized current through electrode E12 decreases toward 0%. As a result, the stimulation region 56 moves from its initial position adjacent electrode E12 to a subsequent position between electrodes E10 and E11 (shown as a dashed circle).

As the joystick 40 is moved rearward, causing electrodes E13 and E14 to be included within the stimulating electrode group 54, and electrode E12 to be excluded from the stimulating electrode group 54, the fractionalized current through each of electrode E13 and E14 increases toward 50%, while the fractionalized current through electrode E12 decreases toward 0%. As a result, the stimulation region 56 moves from its initial position adjacent electrode E12 to a subsequent position between electrodes E13 and E14 (shown as a dashed circle).

Figure 9:
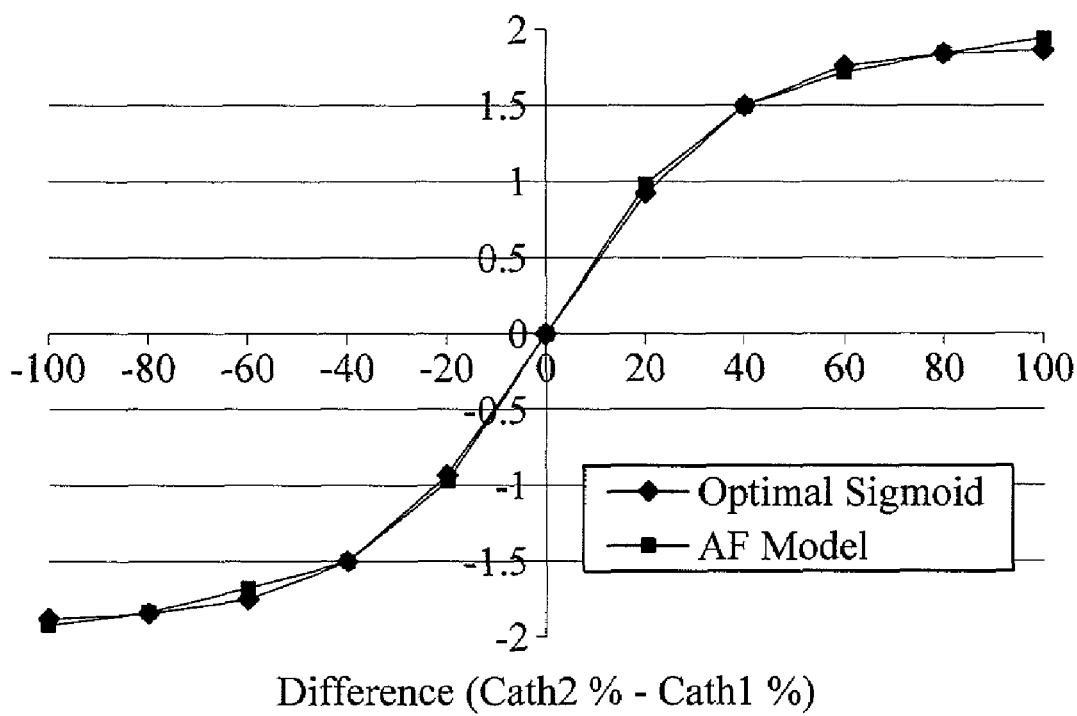
FIG. 9 is a diagram illustrating the position the stimulation region in tissue plotted as a function of fractionalized current between two cathodes.

Thus, based on the foregoing, it can be appreciated that electrical current is shifted between two cathodes in incremental steps. Significantly, the electrical current is shifted between the two electrodes, so that the stimulation region is uniformly displaced relative to the tissue over the incremental steps. Based on a computational model, it has been recognized that uniform step movements as a function of fractionalized current between two cathodes do not yield uniform step movements in the stimulation region—but rather yield step movements in the stimulation region that roughly resemble an optimal sigmoid function, as illustrated in FIG. 9. Thus, movement of the stimulation region relative to tissue can be simplistically expressed by the following closed-form optimized sigmoid:

$$STIM_{pos} = 3.7856\left(\frac{1}{1 + 1.00134 e^{\frac{I_{c2}-I_{c1}}{-18.7684}}}\right) - 1.89667,$$

where $STIM_{pos}$ is the rostrocaudal position of the stimulation region in millimeters, $I_{c2}$ is the fractionalized current flowing through the second cathode, and $I_{c1}$ is the fractionalized current flowing through the first cathode.

Solving for the fractionalized current between the two cathodes as a function of desired position of the stimulation region, provides:

$$I_{c2} - I_{c1} = 18.7684 \ln\left(\frac{3.7856 - STIM_{pos}}{1.00134 * STIM_{pos}}\right)$$

Assuming that the sum of the fractionalized currents $I_{c2}$ and $I_{c1}$ flowing through the two cathodes is 100%, the fractionalized current $I_{c2}$ and $I_{c1}$ can be readily solved for any desired position of the stimulation region. For example, assuming a 4 mm distance between the two cathodes, and assuming that the range of movement of the stimulation region will be slightly less than 4 mm due to contribution of the anode(s), the stimulation region can be displaced using 20 fractionalized current steps (21 fractionalized current states) at a uniform step size of 187.5 μm between positions of the stimulation region, as illustrated in FIG. 10.

Thus, it can be appreciated that the fractionalized electrical current between the two cathodes is incrementally shifted within a range (in this case, from a 100%/0% between the cathodes to a 0%/100% between the cathodes) in accordance with a sigmoid function of the position of the stimulation region. In this manner, the position of the stimulation region will move approximately the same with each increment in the fractionalized current. It should be appreciated that while the fractionalized current between cathodes has been described as being incrementally shifted in accordance with an optimum sigmoid function, the fractionalized current between cathodes can be incrementally shifted in accordance with a sigmoid-like function, i.e., a function that generally resembles that of FIG. 10, but does not strictly conform to an optimal sigmoid function. Preferably, whatever function is used to incrementally shift the fractionalized current between cathodes, uniformity in the displacement of the stimulation region is maximized.

Figure 10:
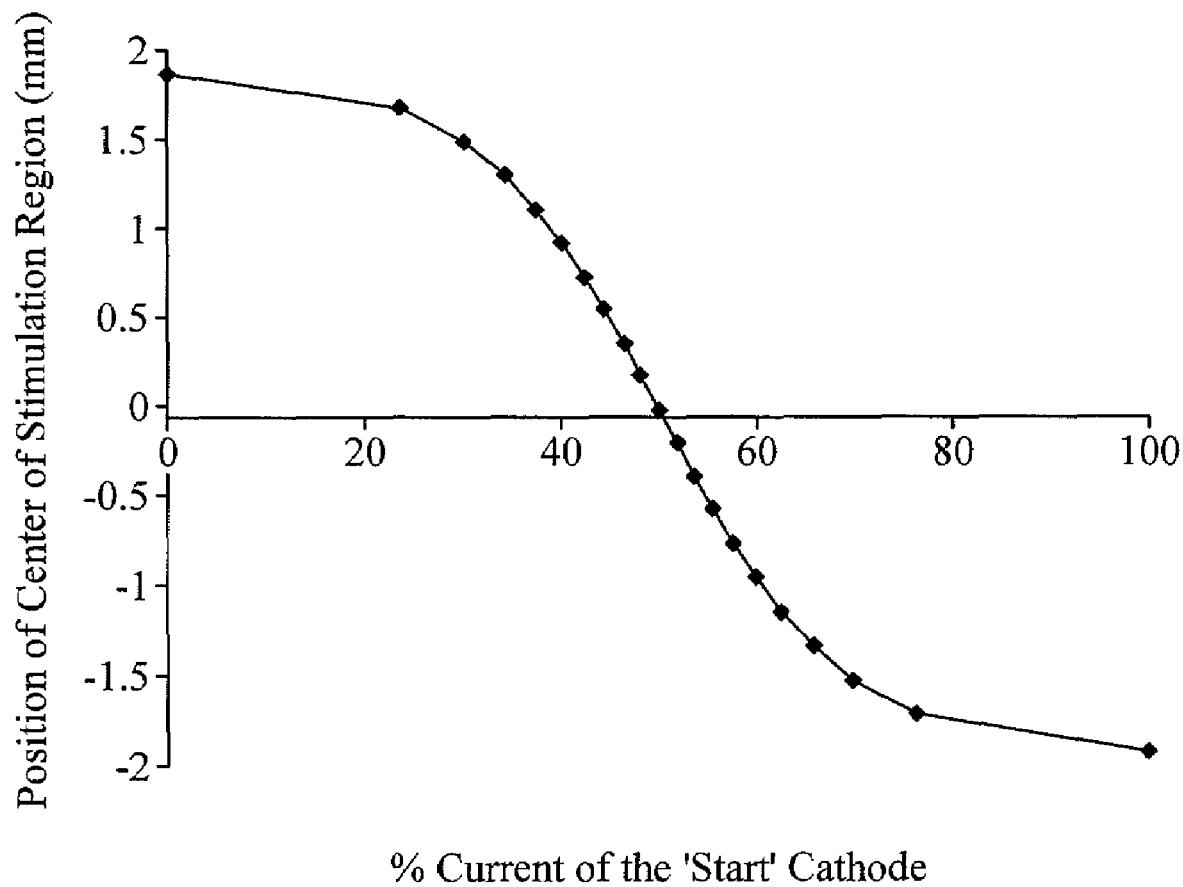
FIG. 10 is a diagram illustrating fractionalized current in a cathode plotted as a function of the position of the stimulation region in tissue, wherein the current has been shifted in non-uniform steps to generate movement of the stimulation region in uniform steps.

As can be seen from FIG. 10, the fractionalized current steps at boundaries of the range are greater than fractionalized current steps at the center of the range. In some embodiments, the smallest fractionalized electrical current step is equal to or less than 5%, while the greatest fractionalized electrical current step is equal to greater than 10%. In other embodiments, the smallest fractionalized electrical current step is equal to or less than 2%, while the greatest fractionalized electrical current step is equal to greater than 20%. In the exemplary embodiment of FIG. 10, the smallest fractionalized current step is approximately 2% and the greatest fractionalized current step is approximately 23%.

Based on the sigmoid function illustrated in FIG. 10, a navigation table, which contains a series of cathodes states and corresponding fractionalized current values, can be created as shown in FIG. 11. Thus, fractionalized electrical current can be shifted between two cathodes by respectively incrementing through the cathode states of the navigation table. As can be seen, the fractionalized current values of the navigation table gradually and non-uniformly change, and in the illustrated embodiment, reflects the fractionalized current steps illustrated in FIG. 10. Thus, the difference between adjacent fractionalized values in the navigation table at boundaries of a range (in this case, the fractionalized values 100/0 to 0/100) are greater than the differences between adjacent values in the navigation table at a center of the range. In some embodiments, the smallest difference between adjacent values in the navigation table is equal to or less than 5% and the greatest difference between adjacent values in the navigation table is equal to or greater than 10%. In other embodiments, the smallest difference between adjacent values in the navigation table is equal to or less than 2% and the greatest difference between adjacent values in the navigation table is equal to or greater than 20%. In the navigation table illustrated in FIG. 11, the smallest difference between adjacent values is 2% (steps between states 6-16) and the greatest difference between adjacent state values is 23% (steps between states 1-2 and states 20-21). Thus, it can be appreciated that the navigation table of FIG. 11 can be used to shift fractionalized electrical current between any two cathodes that are separated by 4 mm.

For example, referring back to FIG. 5, current can be gradually shifted upward from electrode E12 (as cathode 1) to electrode E11 (as cathode 2) by incrementing from state 1 (100/0 split; i.e., 100% on electrode E12 and 0% on electrode E11) to state 21 (0/100 split; i.e., 0% on electrode E12 and 100% on electrode E11). Similarly, current can be gradually shifted downward from electrode E12 (as cathode 1) to electrode E13 (as cathode 2) by incrementing from state 1 (100/0 split; i.e., 100% on electrode E12 and 0% on electrode E13) to state 21 (0/100 split; i.e., 0% on electrode E12 and 100% on electrode E13).

Referring back to FIG. 6, current can be gradually shifted upward from electrode E12 (as cathode 1) to electrode E11 (as cathode 2) by incrementing from state 11 (50/50 split; i.e., 50% on electrode E12 and 50% on electrode E11) to state 21 (0/100 split; i.e., 0% on electrode E12 and 100% on electrode E11), and then upward from electrode E11 (as cathode 1) to electrode E10 (as cathode 2) by incrementing from state 1 (100/0 split; 100% on electrode E11 and 0% on electrode E10) to state 11 (50/50 split; i.e., 50% on electrode E11 and 50% on electrode E10). Similarly, current can be gradually shifted downward from electrode E11 (as cathode 1) to electrode E12 (as cathode 2) by incrementing from state 11 (50/50 split; i.e., 50% on electrode E11 and 50% on electrode E12) to state 21 (0/100 split; i.e., 0% on electrode E11 and 100% on electrode E12), and then downward from electrode E12 (as cathode 1) to electrode E13 (as cathode 2) by incrementing from state 1 (100/0 split; 100% on electrode E12 and 0% on electrode E13) to state 11 (50/50 split; i.e., 50% on electrode E12 and 50% on electrode E13).

Referring back to FIG. 7, current can be gradually shifted upward from electrode E12 (as cathode 1) to electrode E11 (as cathode 2) by incrementing from state 11 (50/50 split; i.e., 25% on electrode E12 and 25% on electrode E11) to state 21 (0/100 split; i.e., 0% on electrode E12 and 50% on electrode E11), and then upward from electrode E11 (as cathode 1) to electrode E10 (as cathode 2) by incrementing from state 1 (100/0 split; i.e., 50% on electrode E11 and 0% on electrode E10) to state 11 (50/50 split; i.e., 50% on electrode E11 and 50% on electrode E10). Similarly, current can be gradually shifted downward from electrode E11 (as cathode 1) to electrode E12 (as cathode 2) by incrementing from state 11 (50/50 split; i.e., 25% on electrode E11 and 25% on electrode E12) to state 21 (0/100 split; i.e., 0% on electrode E11 and 50% on electrode E12), and then downward from electrode E12 (as cathode 1) to electrode E13 (as cathode 2) by incrementing from state 1 (100/0 split; i.e., 50% on electrode E12 and 0% on electrode E13) to state 11 (50/50 split; i.e., 25% on electrode E12 and 25% on electrode E13). Because the initial and end fractionalized current values for the left and right columns of cathodes are the same, in an identical manner, current can be gradually shifted upward from electrode E4 to electrode E3, and then upward from electrode E3 to electrode E2, or downward from electrode E3 to electrode E4, and then downward from electrode E4 to electrode E5. It should be appreciated, however, that even if different initial and end fractionalized values are used for the two columns of cathodes, the same navigation table can be applied independently to the electrode columns by using different initial and end states of the navigation table for the electrode columns.

A modified navigation table can be used to implement the current shifting illustrated in FIG. 8. In particular, the navigation table illustrated in FIG. 12, which splits the current shifted from cathode 1 between cathodes 2 and 3, can be used. Thus, current can be gradually shifted upward from electrode E12 (as cathode 1) to electrodes E10, E11 (as cathodes 2 and 3) by incrementing from state 1 (100/0 split; i.e., 100% on electrode E12 and 0% each on electrodes E10, E11) to state 21 (0/100 split; i.e., 0% on electrode E12 and 50% each on electrodes E0, E11). Similarly, current can be gradually shifted downward from electrode E12 (as cathode 1) to electrodes E13, E15 (as cathodes 2 and 3) by incrementing from state 1 (100/0 split; i.e., 100% on electrode E12 and 0% each on electrodes E13, E14) to state 21 (0/100 split; i.e., 0% on electrode E12 and 50% each on electrodes E13, E14). The same navigation table can be used to shift current from two cathodes to a single cathode, e.g., downward from electrodes E10, E11 to electrode E12, or upward from electrodes E13, E14 to electrode E12.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of operating a tissue stimulation system, comprising:
   placing an array of electrodes in contact with tissue of a patient;
   conveying an electrical current within the electrode array, thereby creating a stimulation region in the tissue; and
   shifting electrical current between cathodes of the electrode array in pre-calculated incremental steps over a range, wherein the incremental steps at boundaries of the range are greater than the incremental steps at a center of the range to displace the stimulation region at substantially uniform distances over the incremental steps.

2. The method of claim 1, wherein the electrical current is shifted in accordance with a sigmoid function of a position of the stimulation region.

3. The method of claim 1, wherein the electrical current is shifted between equal numbers of cathodes.

4. The method of claim 1, wherein the electrical current is shifted between unequal numbers of cathodes.

5. The method of claim 1, wherein the electrical current is shifted between only two cathodes.

6. The method of claim 1, wherein the electrical current is fractionalized, and a smallest incremental step is equal to or less than five percent and a greatest incremental step is equal to or greater than ten percent.

7. The method of claim 1, wherein the electrical current is fractionalized, and a smallest incremental step is equal to or less than two percent and a greatest incremental step is equal to or greater than twenty percent.

8. The method of claim 1, further comprising accessing a navigation table containing a series of states and corresponding electrical current values for the cathodes, wherein the electrical current is shifted by respectively incrementing through the states.

9. The method of claim 1, wherein the tissue is neural tissue.

10. The method of claim 1, wherein the incremental steps are non-uniform.

11. The method of claim 1, further comprising:
implanting the electrode array adjacent the tissue;
configuring a controller that generates an electrical current to be delivered to the electrode array;
selecting an electrode configuration based on a therapeutic effect of the stimulation region as the electrical current is shifted between cathodes; and
programming the controller with the electrode configuration.

12. A method of operating a tissue stimulation system, comprising:
placing an array of electrodes in contact with tissue of a patient;
conveying an electrical current within the electrode array, thereby creating a stimulation region in the tissue; and
shifting electrical current between cathodes of the electrode array in incremental steps over a range in accordance with a sigmoid function of a position of the stimulation region, wherein the incremental steps at boundaries of the range are greater than the incremental steps at a center of the range.

13. The method of claim 12, wherein the sigmoid function is an optimum sigmoid function.

14. The method of claim 12, wherein the electrical current is shifted between equal numbers of cathodes.

15. The method of claim 12, wherein the electrical current is shifted between unequal numbers of cathodes.

16. The method of claim 12, wherein the electrical current is shifted between only two cathodes.

17. The method of claim 12, wherein the electrical current is fractionalized, and a smallest incremental step is equal to or less than five percent and a greatest incremental step is equal to or greater than ten percent.

18. The method of claim 12, wherein the electrical current is fractionalized, and a smallest incremental step is equal to or less than two percent and a greatest incremental step is equal to or greater than twenty percent.

19. The method of claim 12, further comprising accessing a navigation table containing a series of states and corresponding electrical current values for the cathodes, wherein the electrical current is shifted by respectively incrementing through the states.

20. The method of claim 12, wherein the tissue is neural tissue.

21. The method of claim 12, further comprising:
implanting the electrode array adjacent the tissue;
configuring a controller that generates an electrical current to be delivered to the electrode array;
selecting an electrode configuration based on a therapeutic effect of the stimulation region as the electrical current is shifted between cathodes; and
programming the controller with the electrode configuration.

22. A method of operating a tissue stimulation system, comprising:
placing an array of electrodes in contact with tissue of a patient;
conveying an electrical current within the electrode array, thereby creating a stimulation region in the tissue;
accessing a navigation table containing a series of states and corresponding gradually and non-uniformly changing electrical current values, wherein differences between the electrical current values of adjacent states in the navigation table at boundaries of a range of states are greater than differences between adjacent electrical current values of adjacent states in the navigation table at a center of the range of states; and
shifting electrical current between cathodes of the electrode array by incrementing through the states of the navigation table.

23. The method of claim 22, wherein the electrical current is shifted between equal numbers of cathodes.

24. The method of claim 22, wherein the electrical current is shifted between unequal numbers of cathodes.

25. The method of claim 22, wherein the electrical current is shifted between only two cathodes.

26. The method of claim 22, wherein the electrical current values are fractionalized, and a smallest difference between adjacent states in the navigation table is equal to or less than five percent and a greatest difference between adjacent states in the navigation table is equal to or greater than ten percent.

27. The method of claim 22, wherein the electrical current values are fractionalized, and a smallest difference between adjacent states in the navigation table is equal to or less than two percent and a greatest difference between adjacent states in the navigation table is equal to or greater than twenty percent.

28. The method of claim 22, wherein the tissue is neural tissue.

29. The method of claim 22, further comprising:
implanting the electrode array adjacent the tissue;
configuring a controller that generates an electrical current to be delivered to the electrode array;
selecting an electrode configuration based on a therapeutic effect of the stimulation region as the electrical current is shifted between the two electrodes; and
programming the controller with the electrode configuration.

* * * * *